United States Patent [19]

Gatten

[11] Patent Number: 5,592,948

[45] Date of Patent: Jan. 14, 1997

[54] SELF CONTAINED VIAL FOR DRAWING, STORING, SEALING AND IDENTIFYING A FLUID SAMPLE

[76] Inventor: Ronald A. Gatten, 2794 Calle Allegre, Pleasanton, Calif. 94566

[21] Appl. No.: 504,344

[22] Filed: Jul. 19, 1995

Related U.S. Application Data

[63] Continuation of Ser. No. 188,290, Jan. 28, 1994, abandoned.

[51] Int. Cl.$^6$ ....................................... A61B 5/00
[52] U.S. Cl. ........................................... 128/763; 128/760
[58] Field of Search ...................... 128/760, 763, 128/764, 765; 604/132, 133, 187, 189, 190, 201, 203, 212, 214, 216, 905

[56] References Cited

U.S. PATENT DOCUMENTS

| | | | |
|---|---|---|---|
| 2,690,179 | 9/1954 | Fox | 128/765 X |
| 2,950,717 | 8/1960 | Bouet | 604/214 |
| 3,166,030 | 1/1965 | Everett | 604/214 |
| 4,036,232 | 7/1977 | Genese | 128/765 X |
| 4,245,655 | 1/1981 | Patel | 128/765 |
| 4,296,071 | 10/1981 | Weiss et al. | 128/765 X |
| 4,960,676 | 9/1987 | Moulding, Jr. et al. | 604/189 |
| 5,012,845 | 5/1991 | Averette . | |
| 5,045,081 | 9/1991 | Dysarz . | |
| 5,052,403 | 10/1991 | Haber et al. . | |
| 5,071,413 | 12/1991 | Utterberg . | |
| 5,122,129 | 6/1992 | Olson et al. . | |
| 5,148,919 | 9/1992 | Rubin . | |
| 5,224,937 | 7/1993 | Vanderheiden et al. | 406/905 X |
| 5,294,325 | 3/1994 | Liu | 128/763 X |

FOREIGN PATENT DOCUMENTS

| | | | |
|---|---|---|---|
| 468196 | 3/1969 | Switzerland | 604/216 |
| 90/00880 | 2/1990 | WIPO | 604/130 |

OTHER PUBLICATIONS

"Scienceware® Tools For Science From Bel–Art Products", p. 142, undated catalogue page.

"The Target® Answer—Convenience without Evaporation! Introducing Target DP$^{TM}$", *National Scientific Company*, 1993, Catalogue.

*Primary Examiner*—Sam Rimell
*Attorney, Agent, or Firm*—Skjerven, Morrill, MacPherson, Franklin & Friel; Norman R. Klivans

[57] ABSTRACT

A vial assembly integrates the functions of drawing up of a liquid sample through an inlet tube into a storage chamber (a vial), sealing the inlet tube, severing the inlet tube below the seal, identifying the sample for later analysis, and providing sample extraction. Liquid is drawn into the chamber by expanding a collapsed bellows inside the chamber, thereby producing a partial vacuum which draws liquid through the attached inlet tube into the storage chamber. A hot knife sealing shear is then activated to sever the end of the inlet tube from the storage chamber, while simultaneously closing and melting shut the chamber side of the tube. A unique bar code label is on each vial for sample identification.

6 Claims, 2 Drawing Sheets

SELF CONTAINED VIAL FOR DRAWING, STORING, SEALING AND IDENTIFYING A FLUID SAMPLE

This application is a continuation of application Ser. No. 08/188,290, filed Jan. 28, 1994 abandoned.

BACKGROUND OF THE INVENTION

1. Field of the Invention

This invention relates to vials for fluid samples for laboratory testing, and specifically to such a vial having the capability to draw up the fluid, seal the vial, identify the content, and allow for later removal of the sample from the vial.

2. Description of the Prior Art

The functions of taking or drawing up a fluid sample, injecting the sample into a storage chamber (vial), and sealing the vial are commonly undertaken to remove a quantity of the fluid to be sampled from its source and to label and transfer this sample volume to the laboratory for analysis. It is known to use a sampling syringe to draw up the sample, then to inject the sample from the syringe into a sample vial. The vial is then sealed by applying a cap and identified by attaching a label. This prior art includes the rubber bulb type syringe which, when the bulb is manually compressed and then released, causes a vacuum for drawing up of a sample. Syringes used for sampling of liquid are generally piston style with an o-ring seal between the outer wall and the inner actuator piston.

U.S. Pat. No. 5,052,403 discloses (see Abstract): a self-contained, safety blood collection system comprising a shatter-resistant blood collection tube in which a vacuum may be manually established and in which a blood sample, or the like, may be collected by way of a retractable, single ended needle cannula. A piston is relocated from an as-packaged, distal position within the blood collection tube to a proximal position so as to evacuate the tube, whereby the tube is automatically infused with blood under the influence of suction. A controllable fluid valve is formed in an elastomeric stopper, and the stopper is located within the distal end of the blood collection tube, such that the volume and rate at which blood is collected within the tube can be selectively varied. An auxiliary fluid port is formed in the stopper through which successive blood samples may be collected in additional blood collection systems from the same vein puncture.

U.S. Pat. No. 5,045,081 discloses (see Abstract): a vial filling device having a needle cannula fixed to a slidable piston. The slidable piston is held within an elongated hollow barrel by an open spring and latch means. When the elongated hollow barrel is attached to the vial assembly, a lap flange is forced open and the slidable piston is pressed with a thumb, forcing the spring to compress and forcing the needle cannula to penetrate the soft plug in the vial. The blood or other fluid flows through the needle cannula until sufficient blood or other fluid is in the vial. When the vial is suitably filled, the thumb is removed from the slidable piston and the spring pushes the slidable piston in a direction away from the vial thus removing the needle cannula from the vial plug and holding the needle cannula safely inside of the elongated hollow barrel. The elongated hollow barrel is further removed from the plug, the lap flange closes thus enclosing the contaminated needle cannula.

Both of these disclosures use a rigid vial in which a conventional piston is fitted (like that of a syringe). The vials are conventionally sealed with a soft plug. Use of a syringe as in U.S. Pat. No. 5,045,081 causes possible cross contamination, commonly referred to as carry over, associated with the repeated use of a conventional syringe for sample collection. To minimize the cross contamination between samples, the syringe is usually flushed with a cleaning solution between sample extractions. A disposable syringe is sometimes employed in order to insure that cross contamination does not occur.

In another prior art deficiency, if the sample is toxic, protection for the hands and eyes is required while the vial is being handled. Once the liquid sample has been injected into the vial, the vial then is capped. Care must be taken during capping in order to insure that contents are not spilled and that the vial cap is secure. During transfer of the liquid sample from the syringe to the vial and securing of the cap, steps must be taken to avoid inadvertent contact with contaminating materials.

SUMMARY OF THE INVENTION

It is, therefore, a goal of the present invention to improve fluid sample gathering and storage and to simplify the procedure, minimize contamination, and more accurately identify the sample to be analyzed.

In accordance with the invention, an assembly includes a storage chamber inside a housing having e.g. the shape and dimensions of a standard vial and also having an inlet tube attached to one end of the vial. The storage chamber includes in some embodiments a member which is initially collapsed so that, when the member is mechanically expanded, a partial vacuum is produced inside the storage chamber and therefore inside of the inlet tube. (In other embodiments no such member is present and the device operates like a conventional syringe.) The inlet tube conducts fluid into the storage chamber when the end of the tube is inserted into the fluid to be sampled. The fluid can be either gas or liquid; the sealing requirements for a gas are generally more difficult than those for a liquid. The expandable member is e.g. a bellows or bladder which is initially collapsed and is then expanded, causing the sample volume to be drawn up into the storage chamber. Various types of bellows or bladders may be used.

The tube in one embodiment is of a material which can be sheared or punctured as well as sealed such as thermoplastic. The shearing is by e.g. a diagonal cutter, a heated knife edge (which can also seal the tube), or a moving abrasive edge. The puncturing may can be by a penetrating pin. The sealing is alternatively by mechanical crimping of the end of the tube. The crimping of the tube end may take place at elevated temperature and may be followed by the shearing off of the excess tube end.

Also, in one embodiment a filter is located in and a part of the tube; the filter may be separated from the chamber (and hence discarded) along with the excess tube end during the sealing and shearing steps.

The present invention does not require hand transfer of syringe contents to the vial, nor does it require the vial capping by hand. This avoids exposing the operator to toxins associated with accidental contact which can occur during these prior art manual processes. The device does not require the use of a separate syringe; thus, the problem of cross contamination is avoided. Also avoided is the problem of contamination of the sample during these same routine transfer processes, since all components in this embodiment are integrated together and since all the internal volumes are immediately sealed the moment the sample is drawn up. Eliminating sample contamination is becoming increasingly important since analytical instrumentation used today for sample evaluation is capable of routine analysis of parts per billion and even parts per trillion concentration.

A label is attached to and made a part of the sample chamber; the label is a unique identifying mark (bar code) on each individual sample chamber and identifies the associated sample contents located within the sample chamber.

In the prior art, labels are generally applied manually by either writing directly on the vial or else writing on a label which is then attached to the vial. The pre-printed vial identification marking in accordance with the present invention can be read by an associated bar code scanner at the time the sample is introduced into the chamber. Conventional electronics associated with the bar code reader allows the user to correlate the bar code with information regarding the nature of the sample. This correlation between a unique bar code identifier on the vial and recorded information regarding the sample minimizes errors associated with hand applied labeling techniques. Once the vial containing the sample is brought to the laboratory for analysis, the bar code is read and correlative information to the bar code transferred to the laboratory data base. Contents of the coded vial are then removed either by cutting the vial tube or penetrating the vial manually or by automated equipment.

DETAILED DESCRIPTION OF THE INVENTION

Figure 1A:
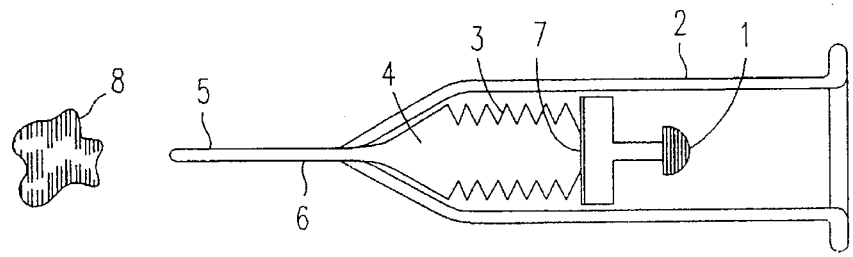
FIGS. 1A, 1B, 1C, 1D, 1E, 1F, 1G show operation of sampling device in accordance with a first embodiment of the invention.
Figure 1B:
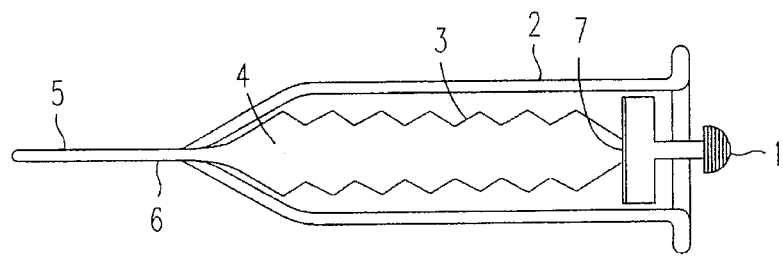

Referring to FIG. 1A (a cross section of a device in accordance with the invention), cylinder 2, the more rigid portion of the structure, is typically of a rigid plastic or metal or glass. Cylinder 2 encloses bellows 3. Bellows 3 is the moveable (expandable) portion of the device and here is in a compressed position. When bellows 3 is extended within cylinder 2, sample chamber 4 expands as shown in FIG. 1B. One end of bellows 3 is connected to an e.g. plastic tube 6 having end 5. Plastic tube 6 protrudes through cylinder 2. Actuator 1 is made of rigid material similar to that of cylinder 2, and is located at the rear portion 7 of bellows 3. Rear portion 7 provides partial vacuum seal against cylinder 2. Prior to the liquid sample 8 being drawn into sample chamber 4, bellows 3 is compressed by actuator 1 as in FIG. 1A, minimizing the volume in chamber 4.

While here cylinder 2 is shown as having a flared end, this is only illustrative. In other embodiments, cylinder 2 has the straight cylindrical sides typical of a standard commercially available autosampler vial (such as from National Scientific Company, Lawrenceville, Ga.), and the dimensions of same, for handling by conventional automated equipment.

Figure 1C:
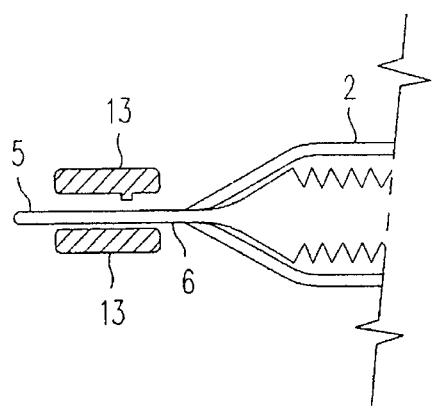
Figure 1E:
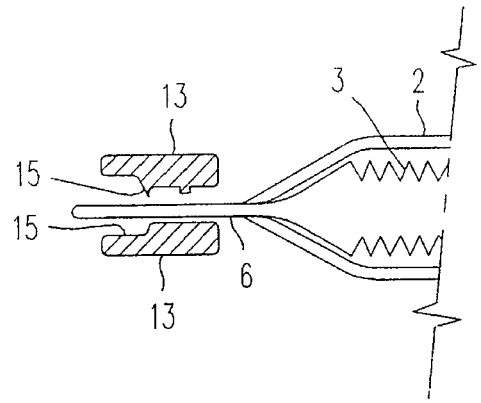
Figure 1D:
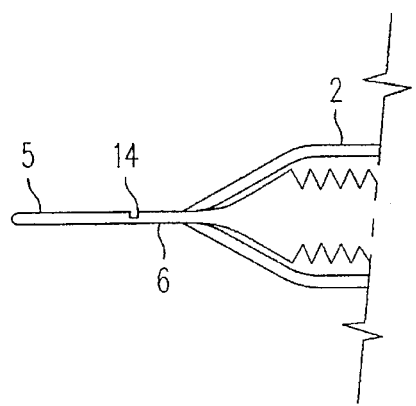

Referring to FIG. 1B, when sample 8 is to be drawn, the tube end 5 is placed into the liquid 8 to be sampled. The bellows 3 is then extended within the cylinder 2, by actuation force on actuator 1 expanding the volume within cylinder 2. The resulting displacement and unfolding of bellows 3, in relation to cylinder 2, creates a vacuum in the chamber 4 and in tube 6, such that a volume of liquid 12 is drawn through the tube end 5 into chamber 4. Once the bellows 3 has been expanded, tube 6 is sealed by mechanical crimping mechanism 13, compressing against tube 6, as shown in FIG. 1C. The crimped section 14 of tube 6 is as shown in FIG. 1D.

Note that a conventional collapsible bladder may be used in place of the bellows.

An alternative sealing and shearing mechanism applies heat to the crimping mechanism jaws to soften the (plastic) tube 6 and allows thermal fusing (sealing) of the tube while it is being crimped. A conventional resistive heating element (not shown) located in the crimping jaws 13 elevates the temperature of the jaws above the fusion melting point of the plastic tube 6.

Figure 1F:
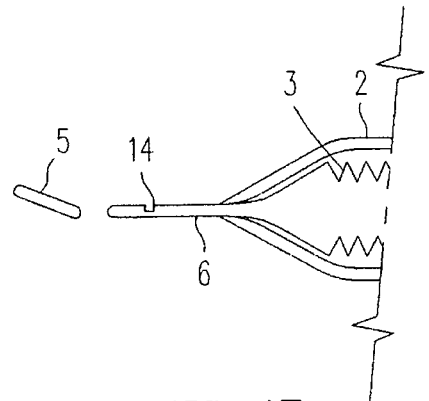

In another version in FIG. 1E, sealing of tube 6 is accompanied by shearing by cutters 15 located on crimping jaws 13 below the point 14 of fusing, thus, as shown in FIG. 1F, allowing the sheared tube end 5 to be removed and discarded from the sealed portion of tube 6 still attached to the cylinder 2 and unfolded bellows 3, so the sealed assembly now has the sample sealed inside.

The crimping/sealing/cutting mechanism(s) typically (but not necessarily) is not attached to the vial, and so typically is a separate device, handheld or other.

Figure 1G:
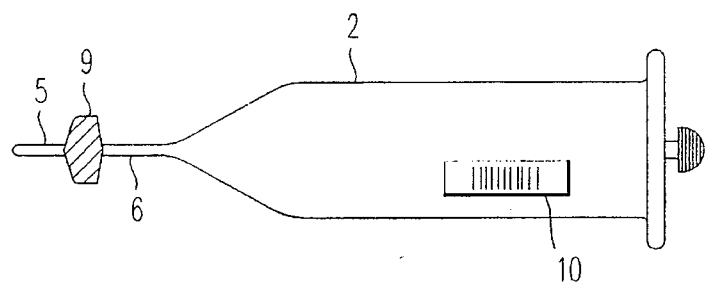

A filter 9 may also be provided in tube 6, as in FIG. 1G. Filter 9 is located so that it is cut off and discarded with tube end 5. Bar code label 10 is affixed to the exterior of cylinder 2.

Figure 2:
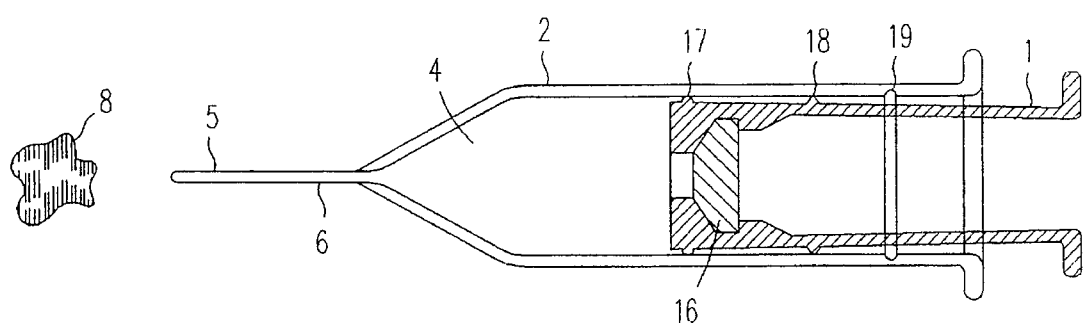
FIG. 2 shows a second embodiment.

An alternative embodiment does not utilize a bellows for sample draw and storage. Referring to FIG. 2 (a cross section of a device in accordance with the invention), cylinder 2, the more rigid portion of the structure, is typically of a rigid plastic or metal or glass. Cylinder 2 encloses a piston type actuator 1. Actuator 1 is the moveable portion of the device. When actuator 1 is extended within cylinder 2, sample chamber 4 expands. One end of sample chamber 4 is connected to a metal tube 6 having end 5. Actuator 1 and associated sealing ring 17 provide a vacuum seal against cylinder 2.

Prior to the sample being drawn into sample chamber 4, actuator 1 is depressed towards tube 6, minimizing the volume in chamber 4. When a sample 8 is to be drawn, the tube end 5 is placed into the liquid sample 8. The actuator is then moved away from tube 6, thereby expanding the volume within cylinder 2. The resulting vacuum created in the chamber 4 and in tube 6 draws a volume of liquid 8 through the tube end 5 and into chamber 4. A locator slot 19 is formed on the interior of cylinder 2. When actuator 1 is extended until locator ring 18 on actuator 1 is adjacent to locator slot 19, the locator ring 18 engages locator slot 19 such that actuator 1 is restricted from further extension. Tube 6 is sealed by mechanical crimping compression of the metal tube 6 as described alone. The sealed assembly now has the sample sealed inside.

To remove the sample for later analysis, the soft septum 16 located in the center of actuator 1 is punctured by an extraction device, such as the needle of an autosampler, and the sample removed. Alternatively, sample removal of the sealed chamber is achieved by shearing the tube 6 between the crimped portion and the sample chamber 2, the actuator 1 is then depressed toward the tube 6, and the sample contents pressed out of the sheared tube 6.

The above description is illustrative and not limiting; further modifications will be apparent to one skilled in the art.

I claim:

1. A method of storing and extracting a fluid in a chamber having two ends and having a tubular portion at a first end defining a port at one end of the tubular portion, the method comprising:

drawing the fluid into said chamber by extending a piston disposed in said chamber;

closing said tubular portion;

providing a septum in said chamber;

penetrating the septum with a hollow needle from a second end of said chamber opposite the first end of said chamber; and extracting the fluid from said chamber through said needle.

2. The method of claim 1, wherein the step of closing comprises crimping.

3. The method of claim 1, wherein the step of closing comprises heat sealing.

4. The method of claim 1, further comprising severing a distal part of said tubular portion after the step of closing.

5. The method of claim 1, wherein the step of drawing includes filtering the fluid.

6. The method of claim 1, further comprising:

providing a bar code on the sample chamber; and scanning said bar code.

\* \* \* \* \*